United States Patent [19]

Deeg et al.

[11] 3,996,627

[45] Dec. 14, 1976

[54] ARTIFICIAL INTRAOCULAR LENS

[75] Inventors: Emil W. Deeg, Woodstock, Conn.; Robert E. Graf; David A. Krohn, both of Southbridge, Mass.

[73] Assignee: American Optical Corporation, Southbridge, Mass.

[22] Filed: Sept. 22, 1975

[21] Appl. No.: 615,276

[52] U.S. Cl. ........................................ 3/13; 106/54; 106/52; 106/47 Q; 106/163; 351/167

[51] Int. Cl.² ........................................ A61F 1/16

[58] Field of Search ........... 106/47 Q, 54, 52; 3/13; 351/159, 163

[56] References Cited

UNITED STATES PATENTS

| | | | |
|---|---|---|---|
| 3,790,260 | 2/1974 | Boyd et al. | 351/159 |
| 3,898,093 | 8/1975 | Faulstich et al. | 106/54 |
| 3,922,728 | 12/1975 | Krasnov | 3/13 |
| 3,925,825 | 12/1975 | Richards et al. | 3/13 |

OTHER PUBLICATIONS

Weyl, W. A. – *Coloured Glasses* – Dawson's of Pall Mall, London (1959) QD 139 G5, pp. 129–131, 229–234.

Troutman, R. C. – "Artiphakia & Aniseikonia" – Am. J. of Ophthalmology 56 (2) Oct. 1963 (pp. 602–639); 3–13.

*Primary Examiner*—Helen M. McCarthy

*Attorney, Agent, or Firm*—H. R. Berkenstock, Jr.; William C. Nealon

[57] ABSTRACT

A chemically durable, inert optical implant lens and glass composition for the manufacture of same.

10 Claims, 2 Drawing Figures

ARTIFICIAL INTRAOCULAR LENS

FIELD OF THE INVENTION

This invention relates to improvements in ophthalmology and more particularly to improvements in artificial intraocular lenses (pseudophakoi) used for the correction of aphakia and re-establishment of binocularity in aphakia.

DISCUSSION OF THE PRIOR ART

Heretofore, pseudophakoi formed of glass have been complicated and ungainly in structure, e.g. comprised of plural elements with sealed air space or buoyancy and/or formed of conventional glass compositions of relatively high density having less than optimum spectral transmission for intraocular applications.

In addition to not adequately simulating the optical absorption of a human crystalline lens, commercial glasses frequently contain significant amounts of toxic and/or radioactive agents, compounds or materials, any one or all of which render these glasses potentially harmful in vivo.

With current lens fixturing techniques obviating the need to strive for weightlessness in situ, the art has, for the most part, turned to the use of biologically inert organic high polymers such as polyethylmethacrylate as lens materials. These materials, while offering the advantage of minimizing toxicity and radioactivity, nevertheless fall short of providing optimum intraocular spectral transmittance.

Accordingly, it is a principal object of this invention to make available to the ophthalmologist and patient an intraocularly implantable lens of glass which is uniquely chemically durable, free of toxicity and harmful radioactivity, of low density for lightness of weight and has a spectral transmission simulating the optical absorption of the human crystalline lens.

SUMMARY OF THE INVENTION

The foregoing object and its corollaries are accomplished by the provision of a novel glass composition of high chemical durability and free of harmful toxic and radioactive substances.

Base glasses which are exemplary but not restrictive to the invention are soda borosilicates and sodium titania silicates. Purified cerium oxide and transition metal oxides are incorporated into these base glasses for simulation of the optical absorption of the crystalline lens.

Details of the invention will become more readily apparent from the following description when taken in conjunction with the accompanying drawings.

IN THE DRAWINGS

FIG. 1 is an illustration, in cross-section, of an artificial intraocular lens in situ, the lens being exemplary of intraocular devices contemplated according to the invention; and FIG. 2 is a spectral transmission chart illustrating transmission properties of examples of glass compositions produced according to the invention and further illustrating, for comparison purposes, the spectral transmission properties of a 51 year-old human crystalline lens.

DESCRIPTION OF THE PREFERRED EMBODIMENTS

Artificial intraocular lenses (pseudophakoi) of various types and configurations, e.g. double convex and plano-convex in either one-piece or plural element structures have been used for the correction of aphakia and re-establishment of binocularity in aphakia. These are exemplary of devices to which glass compositions of the present invention are especially applicable and intended for use.

Figure 1:
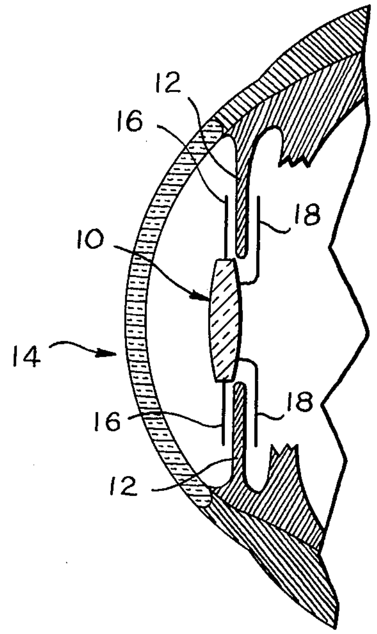

The need for weightlessness in situ, heretofore attempted with plural element lenses having sealed air chambers, has been overcome with iris-clip and iridocapsular fixturing techniques. Iris-clip fixturing is usually used after intracapsular cataract extraction and iridocapsular fixturing after extracapsular extraction. The iris clip lens may also be used following extracapsular surgery and, accordingly, has been depicted in FIG. 1 of the drawings to illustrate a typical lens product of the invention. It should be understood, however, that the invention has similar applicability to all other types of pseudophakoi including the plural element "weightless" lenses.

Lens 10 (FIG. 1) is fixtured to iris 12 of eye 14 with anterior and posterior clips 16 and 18 respectively. These clips may be in the form of loops and/or struts constructed of strands of plastic material, e.g. extruded teflon, or of metal, e.g. platinum, titanium or tantalum wire. Those interested in details of intraocular lens fixturing may refer to "Post-Traumatic Artificial Lens Implants (Pseudophakoi) In Children" by C. D. Binkhorst, M. H. Gobin and P. A. Leonard; *British Journal of Ophthalmology*, Volume 53, No. 8, pages 518–529, August 1969 and/or "The Iridocapsular (Two-Loop) Lens and the Iris-Clip (Four-Loop) Lens in Pseudophakia" by Corneleus D. Binkhorst, M.D., O.P., Volume 77, Sept.–Oct., 1973, pages 589–617.

Intraocular lens fixturing will not be discussed in further detail herein since this subject per se does not have particular bearing upon the crux of the present invention.

Whether plano-convex, double convex, plural element and/or other intraocular lenses are to be produced, this invention contemplates the provision of a glass composition which is unique in its characteristics of: low density for lightness of weight; high chemical durability under conditions of intraocular use; freedom from toxicity or harmful radioactivity; and spectral transmission characteristics simulating those of human crystalline lenses particularly with desired ultraviolet absorption.

Exemplary base glasses are soda borosilicates and sodium titania silicates wherein all raw materials, particularly $SiO_2$, are selected to be types which are free of traces of radioactive substances such as uranium oxide. A source for such $SiO_2$ is that produced by pyrolysis of $SiCl_4$ or of tetra-ethyl-ortho-silicate. Conventionally used but potentially radioactive and/or leachable toxic glass forming and fining agents or compounds such as potassium oxide, $As_2O_3$ or $Sb_2O_3$ and lead, cadmium or lithium oxides as well as $P_2O_5$, Te, Se, and Th compounds are avoided.

In order to simulate the optical absorption of the human crystalline lens, cerium oxide and transition metal oxides are incorporated into the aforesaid base glasses with special care being taken to use only highly purified raw materials which are free of traces of radioactive substances.

Glasses of compositions contemplated by this invention may be produced according to standard glass making techniques with raw materials consisting of high purity silica; nitrates of sodium and barium; carbonates of sodium, strontium, calcium and manganese; and oxides of titanium, zirconium, cerium, boron, zinc, iron and copper. It is understood, however, that introduction of impurities listed above is possible if crucibles, stirrers, etc. are not selected properly. Therefore, it is preferred that these items are made of high purity glass maker's platinum and are used only for melting these specific glasses.

Ingredients useful in the formulation of glass compositions according to this invention are given in the following Table:

TABLE I

| | wt. % |
|---|---|
| $SiO_2$ | 38.2 to 70.5 |
| $TiO_2$ | 0 to 24.3 |
| $ZrO_2$ | 0 to 4.5 |
| $La_2O_3$ | 0 to 2.1 |
| $B_2O_3$ | 0 to 10 |
| $Al_2O_3$ | 0 to 4.8 |
| $Fe_2O_3$ | 0 to 2.2 |
| ZnO | 0 to 1.7 |
| CaO | 0 to 1 |
| $CaF_2$ | 0 to .6 |
| SrO | 0 to 1.2 |
| MnO | .1 to 3 |
| BaO | 3.5 to 5.5 |
| $Na_2O$ | 6.6 to 18.6 |
| $CeO_2$ | 0.3 to 5 |
| $K_2O$ | 0 to 4 |
| CuO | 0 to .05 |

Compositions suitable for artificial intraocular lenses are given in the following table:

TABLE II

| | A | B | C | D | E | F | G | H | I | J |
|---|---|---|---|---|---|---|---|---|---|---|
| $SiO_2$ | 70.50 | 38.3 | 38.3 | 38.3 | 38.3 | 38.3 | 38.7 | 38.3 | 38.7 | 71.0 |
| $TiO_2$ | — | 24.3 | 22.3 | 23.3 | 23.8 | 23.8 | 23.8 | 23.8 | 23.8 | — |
| $ZrO_2$ | — | 4.1 | 4.1 | 4.1 | 4.1 | 4.5 | 4.5 | 4.5 | 4.5 | — |
| $La_2O_3$ | — | 1.4 | 1.4 | 1.4 | 1.4 | 1.9 | 1.9 | 2.1 | 2.1 | — |
| $B_2O_3$ | 10.0 | 2.9 | 2.9 | 2.9 | 2.9 | 2.9 | 2.9 | 2.9 | 2.9 | 8.5 |
| $Al_2O_3$ | 4.8 | — | — | — | — | — | — | — | — | 4.3 |
| $Fe_2O_3$ | — | — | 2.0 | 1.0 | 0.5 | 0.3 | 0.1 | 0.3 | 0.1 | 2.2 |
| ZnO | — | 1.7 | 1.7 | 1.7 | 1.7 | 1.7 | 1.7 | 1.7 | 1.7 | — |
| CaO | — | 1.0 | 1.0 | 1.0 | 1.0 | 1.0 | 1.0 | 1.0 | 1.0 | — |
| $CaF_2$ | 0.6 | — | — | — | — | — | — | — | — | — |
| SrO | — | 1.2 | 1.2 | 1.2 | 1.2 | 1.2 | 1.2 | 1.2 | 1.2 | — |
| MnO | — | — | 2.0 | 1.0 | 0.5 | 0.3 | 0.1 | 0.3 | 0.1 | 3.0 |
| BaO | 4.0 | 5.5 | 3.5 | 4.5 | 5.0 | 5.0 | 5.0 | 5.0 | 5.0 | 3.5 |
| $Na_2O$ | 6.6 | 18.6 | 18.6 | 18.6 | 18.6 | 18.6 | 18.6 | 18.6 | 18.6 | 7.1 |
| $CeO_2$ | 3.5 | 1.0 | 1.0 | 1.0 | 1.0 | 0.5 | 0.5 | 0.3 | 0.3 | — |
| $K_2O$ | — | — | — | — | — | — | — | — | — | 0.4 |
| CuO | — | — | — | — | — | — | — | — | — | — |

| | K | L | M | N | O | P | Q | R | S |
|---|---|---|---|---|---|---|---|---|---|
| $SiO_2$ | 38.3 | 38.3 | 38.1 | 38.5 | 38.7 | 38.4 | 38.3 | 38.2 | 38.15 |
| $TiO_2$ | 23.8 | 23.8 | 23.8 | 23.8 | 23.8 | 23.8 | 23.8 | 23.8 | 23.8 |
| $ZrO_2$ | 4.5 | 4.5 | 4.5 | 4.5 | 4.5 | 4.5 | 4.5 | 4.5 | 4.5 |
| $La_2O_3$ | — | — | — | — | — | — | — | — | — |
| $B_2O_3$ | 2.9 | 2.9 | 2.9 | 2.9 | 2.9 | 2.9 | 2.9 | 2.9 | 2.9 |
| $Al_2O_3$ | — | — | — | — | — | — | — | — | — |
| $Fe_2O_3$ | 0.3 | 0.3 | 0.4 | 0.2 | 0.1 | 0.3 | 0.4 | 0.5 | 0.5 |
| ZnO | 1.7 | 1.7 | 1.7 | 1.7 | 1.7 | 1.7 | 1.7 | 1.7 | 1.7 |
| CaO | 1.0 | 1.0 | 1.0 | 1.0 | 1.0 | 1.0 | 1.0 | 1.0 | 1.0 |
| $CaF_2$ | — | — | — | — | — | — | — | — | — |
| SrO | 1.2 | 1.2 | 1.2 | 1.2 | 1.2 | 1.2 | 1.2 | 1.2 | 1.2 |
| MnO | 0.3 | 0.3 | 0.4 | 0.2 | 0.1 | 0.2 | 0.2 | 0.2 | 0.2 |
| BaO | 5.0 | 5.0 | 5.0 | 5.0 | 5.0 | 5.0 | 5.0 | 5.0 | 5.0 |
| $Na_2O$ | 18.6 | 16.0 | 18.6 | 18.6 | 18.6 | 18.6 | 18.6 | 18.6 | 18.6 |
| $CeO_2$ | 2.4 | 5.0 | 2.4 | 2.4 | 2.4 | 2.4 | 2.4 | 2.4 | 2.4 |
| $K_2O$ | — | — | — | — | — | — | — | — | — |
| CuO | — | — | — | — | — | — | — | — | 0.05 |

In reductions to practice of the invention, each of compositions A–S (Table II) were produced in a clean environment by thoroughly mixing their designated raw materials and transferring the mix in 300–400 gram portions into a preheated platinum crucible of 0.5 liter capacity. The crucible was preheated to approximately 1320° C in an electric furnace.

After filling the crucible, its temperature was raised to approximately 1370° C and held for approximately 1 hour, lowered to approximately 1150° C and held for approximately 2 hours. The resulting glass melt was stirred for approximately ¼ hour and cast at approximately 1150° C into a slab of approximately 15 cm × 10 cm × 1 cm.

Lenses were then cut, ground and polished from the cast glass slab. Those skilled in the art will readily appreciate that the aforesaid glasses may be cast into other shapes such as the shape of a rod or as individual lens blanks and that various other modifications and adaptations of the aforesaid glass-making and lens-forming procedures may be made to suit particular requirements.

Figure 2:
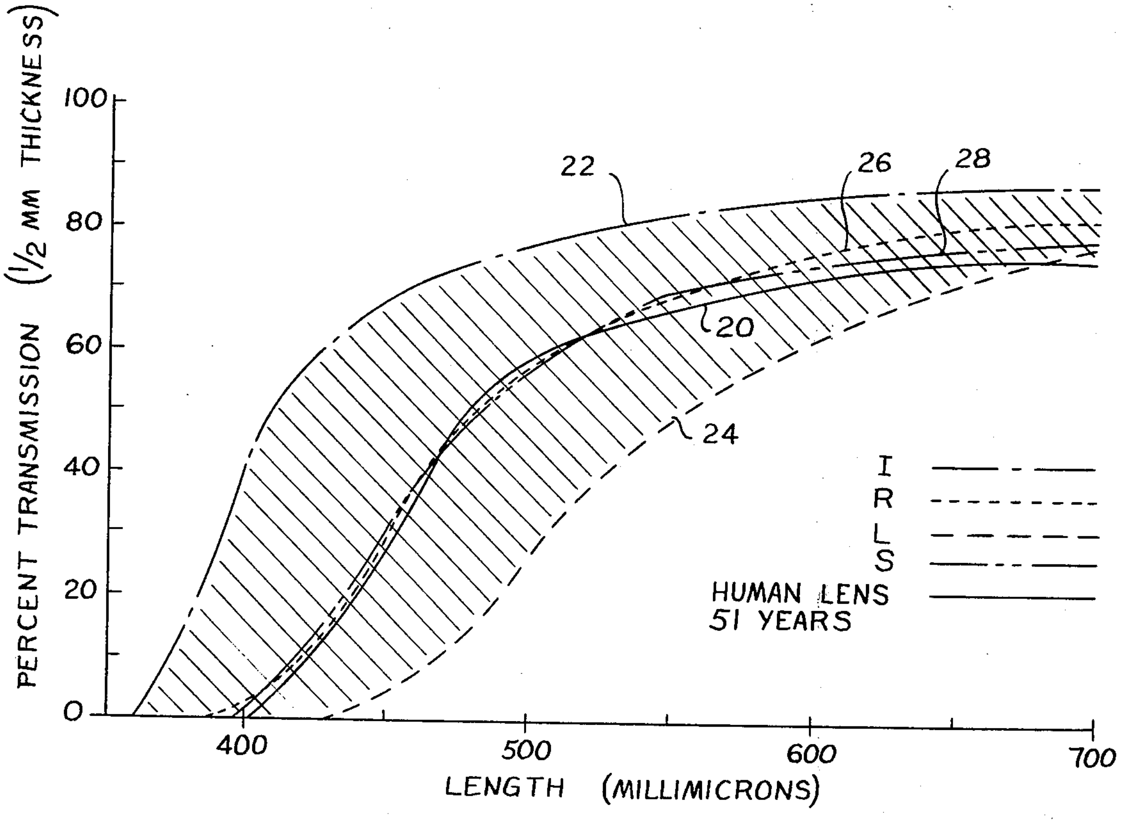

Referring more particularly to FIG. 2 of the drawings, the curve 20 which is depicted with an unbroken line, graphically represents percent spectral transmission of the average human crystalline lens of age 51 years, its absorption of ultraviolet being apparent.

The spectral transmissions of glasses of compositions I and L (Table II) taken in ½ mm thickness each have been plotted with curves 22 and 24 respectively illustrating their simulation of optical absorption of the human crystalline lens, the human lens of equivalent power also being of approximately ½ mm in optical center thickness. It should be understood that while crystalline lenses of persons younger and older than 51 years may respectively vary somewhat upwardly and downwardly in percent transmission from those represented by curve 20, spectral transmission between those represented by curves 22 and 24 are closely approximative of lenses of all normal human eyes.

All glasses of compositions A–H, J–K and M–S of Table II have percent spectral transmission characteristics which may be represented by curves lying between curves 22 and 24, i.e. within the area of cross-hatching in FIG. 2.

Curves 26 and 28 of FIG. 2 represent plots of the spectral transmission of glasses of compositions R and S (Table II). These spectral transmission curves lie nearly centrally of outer boundaries of the aforesaid envelope of cross-hatching and represent spectral transmission characteristics substantially identical to those of the 51 year-old human lens (curve 20). Thus, it has been demonstrated that by selection from the compositions of Table II, simulation of the absorption characteristics of the human crystalline lens may be uniquely accomplished in pseudophakia.

Glasses formed of the compositions of Table II, in addition to having spectral transmission characteristics simulating those of human crystalline lenses and being of high chemical durability with freedom from toxicity and radioactivity, are of low density weighing approximately from 2.46 to 3.05 g/cc.

A lens of edge thickness 0.12 mm, center thickness ½ mm and diameter 5.0 mm will weigh approximately 15 mg in air. Indices of refraction of the aforesaid glasses range from 1.502 and 1.717 with coefficients of expansion (°C$^{-1}$) being approximately 40 × $10^{-7}$.

We claim:

1. A glass adaptable to use in the manufacture of artificial intraocular lenses consisting essentially of the following ingredients in the range of weight percent:

| | |
|---|---|
| $SiO_2$ | 38.1 to 38.7 |
| $TiO_2$ | 22.3 to 23.8 |
| $ZrO_2$ | 4.1 to 4.5 |
| $La_2O_3$ | 0 to 2.1 |
| $B_2O_3$ | 2.9 |
| $Fe_2O_3$ | 2.0 |
| ZnO | 1.7 |
| CaO | 1.0 |
| SrO | 1.2 |
| MnO | .1 to 2.0 |
| BaO | 3.5 to 5.0 |
| $Na_2O$ | 18.6 |
| $CeO_2$ | 0.3 to 5 |
| CuO | 0 to .05 |

said glass having spectral transmission characteristics simulating the optical absorption of human crystalline lenses being of high chemical durability with freedom from toxicity and radioactivity, of low density from about 2.46 to 3.05 g/cc and having a coefficient of expansion (°C$^{-1}$) approximately 40 33 $10^{-7}$.

2. A glass according to claim 1 wherein the following ingredients are present by weight percent:

| | |
|---|---|
| $SiO_2$ | 38.2 |
| $TiO_2$ | 23.8 |
| $ZrO_2$ | 4.5 |
| $B_2O_3$ | 2.9 |
| $Fe_2O_3$ | 0.5 |
| ZnO | 1.7 |
| CaO | 1.0 |
| SrO | 1.2 |
| MnO | 0.2 |
| BaO | 5.0 |
| $Na_2O$ | 18.6 |
| $CeO_2$ | 2.4. |

3. A glass according to claim 1 wherein the following ingredients are present by weight percent:

| | |
|---|---|
| $SiO_2$ | 38.15 |
| $TiO_2$ | 23.8 |
| $ZrO_2$ | 4.5 |
| $B_2O_3$ | 2.9 |
| $Fe_2O_3$ | 0.5 |
| ZnO | 1.7 |
| CaO | 1.0 |
| SrO | 1.2 |
| MnO | 0.2 |
| BaO | 5.0 |
| $Na_2O$ | 18.6 |
| $CeO_2$ | 2.4 |
| CuO | 0.05. |

4. A glass according to claim 1 wherein the following ingredients are present by weight percent:

| | |
|---|---|
| $SiO_2$ | 38.7 |
| $TiO_2$ | 23.8 |
| $ZrO_2$ | 4.5 |
| $La_2O_3$ | 2.1 |
| $B_2O_3$ | 2.9 |
| $Fe_2O_3$ | 0.1 |
| ZnO | 1.7 |
| CaO | 1.0 |
| SrO | 1.2 |
| MnO | 0.1 |
| BaO | 5.0 |
| $Na_2O$ | 18.6 |
| $CeO_2$ | 0.3. |

5. A glass according to claim 1 wherein the following ingredients are present by weight percent:

| | |
|---|---|
| $SiO_2$ | 38.3 |
| $TiO_2$ | 23.8 |
| $ZrO_2$ | 4.5 |
| $B_2O_3$ | 2.9 |
| $Fe_2O_3$ | 0.3 |
| ZnO | 1.7 |
| CaO | 1.0 |
| SrO | 1.2 |
| MnO | 0.3 |
| BaO | 5.0 |
| $Na_2O$ | 16.0 |
| $CeO_2$ | 5.0 |

6. A glass lens being of high chemical durability with freedom from toxicity and radioactivity, of low density from about 2.46 to 3.05 g/cc and having a coefficient of expansion (°C$^{-1}$) approximately 40 × $10^{-7}$ suitable for intraocular implantation and having spectral transmission characteristics simulating the optical absorption of human crystalline lenses wherein the composition of the glass consists essentially of the following ingredients in the range of weight percent:

| | |
|---|---|
| $SiO_2$ | 38.1 to 38.7 |
| $TiO_2$ | 22.3 to 23.8 |
| $ZrO_2$ | 4.1 to 4.5 |
| $La_2O_3$ | 0 to 2.1 |
| $B_2O_3$ | 2.9 |
| $Fe_2O_3$ | 0 to 2.0 |
| ZnO | 1.7 |
| CaO | 1.0 |
| SrO | 1.2 |
| MnO | .1 to 2.0 |

-continued

| | |
|---|---|
| BaO | 3.5 to 5.0 |
| $Na_2O$ | 18.6 |
| $CeO_2$ | 0.3 to 5 |
| CuO | 0 to .05 |

7. A lens according to claim 6 wherein the composition of the glass consists of the following ingredients by weight percent:

| | |
|---|---|
| $SiO_2$ | 38.2 |
| $TiO_2$ | 23.8 |
| $ZrO_2$ | 4.5 |
| $B_2O_3$ | 2.9 |
| $Fe_2O_3$ | 0.5 |
| ZnO | 1.7 |
| CaO | 1.0 |
| SrO | 1.2 |
| MnO | 0.2 |
| BaO | 5.0 |
| $Na_2O$ | 18.6 |
| $CeO_2$ | 2.4. |

8. A lens according to claim 6 wherein the composition of the glass consists of the following ingredients by weight percent:

| | |
|---|---|
| $SiO_2$ | 38.15 |
| $TiO_2$ | 23.8 |
| $ZrO_2$ | 4.5 |
| $B_2O_3$ | 2.9 |
| $Fe_2O_3$ | 0.5 |
| ZnO | 1.7 |
| CaO | 1.0 |
| SrO | 1.2 |
| MnO | 0.2 |
| BaO | 5.0 |
| $Na_2O$ | 18.6 |

-continued

| | |
|---|---|
| $CeO_2$ | 2.4 |
| CuO | 0.05. |

9. A lens according to claim 6 wherein the compositions of the glass consists of the following ingredients by weight percent:

| | |
|---|---|
| $SiO_2$ | 38.7 |
| $TiO_2$ | 23.8 |
| $ZrO_2$ | 4.5 |
| $La_2O_3$ | 2.1 |
| $B_2O_3$ | 2.9 |
| $Fe_2O_3$ | 0.1 |
| ZnO | 1.7 |
| CaO | 1.0 |
| SrO | 1.2 |
| MnO | 0.1 |
| BaO | 5.0 |
| $Na_2O$ | 18.6 |
| $CeO_2$ | 0.3. |

10. A lens according to claim 6 wherein the composition of the glass consists of the following ingredients by weight percent:

| | |
|---|---|
| $SiO_2$ | 38.3 |
| $TiO_2$ | 23.8 |
| $ZrO_2$ | 4.5 |
| $B_2O_3$ | 2.9 |
| $Fe_2O_3$ | 0.3 |
| ZnO | 1.7 |
| CaO | 1.0 |
| SrO | 1.2 |
| MnO | 0.3 |
| BaO | 5.0 |
| $Na_2O$ | 16.0 |
| $CeO_2$ | 5.0. |

* * * * *